(12) United States Patent
Doubrava et al.

(10) Patent No.: US 6,400,793 B2
(45) Date of Patent: Jun. 4, 2002

(54) DETECTOR FOR AN X-RAY COMPUTED TOMOGRAPHY APPARATUS

(75) Inventors: Clemens Doubrava, Bonn; Thomas Von Der Haar, Nuremberg, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/813,502

(22) Filed: Mar. 20, 2001

(30) Foreign Application Priority Data

Mar. 27, 2000 (DE) .......................... 100 15 191

(51) Int. Cl.$^7$ ............................................. G01N 23/00
(52) U.S. Cl. ................................... 378/19; 250/370.09
(58) Field of Search ..................... 378/19; 250/370.09

(56) References Cited

U.S. PATENT DOCUMENTS 6,188,745 B1    2/2001    Gordon

FOREIGN PATENT DOCUMENTS

| DE | 195 02 574 | 8/1996 |
|---|---|---|
| DE | 199 42 919 | 4/2000 |
| WO | WO 98/05980 | 2/1998 |

*Primary Examiner*—Craig E. Church
(74) *Attorney, Agent, or Firm*—Schiff Hardin & Waite

(57) ABSTRACT

A detector for an X-ray computed tomography apparatus has a number of detector elements separated from one another be septa forming a detector line. For improving the efficiency of the detector, the septa are arranged according to the relationship:

$$\{s_k\} = \bigcup_{m=1}^{j}\left\{\bigcup_{p=-z/2}^{z/2}\{p \cdot n_m \cdot D_1\}\right\},$$

wherein $\{S_k\}$ is the total number of septum locations,
  $z \in N$ is the number of channels,
  $D_1$ is the smallest width of a detector element,
  $D_i = n_i D_i$ is the width of the $i^{th}$ subdivision, whereby $i>1$ and $n_i > n_{i-1}$ apply, and
  $j \in N$ is the number of different widths $D_i$.

3 Claims, 3 Drawing Sheets

DETECTOR FOR AN X-RAY COMPUTED TOMOGRAPHY APPARATUS

BACKGROUND OF THE INVENTION

1. Field of the Invention

The present invention is directed to a detector for an X-ray computed tomography apparatus of the type having a number of detector elements of different widths separated from one another by septa, forming a detector line arranged in a direction of a rotational axis of the tomography apparatus, with a number of such detector lines being arranged next to each other, and wherein a predetermined number of channels are provided for acquiring signals generated by the detector elements, with one or more of the detector elements being selectively connectable to respective ones of the channels for acquiring the signals.

2. Description of the Prior Art

Detectors of the above general type are disclosed in German OS 195 02 574 and PCT Application WO 98/05980. They have a number of parallel detector lines that proceed in the direction of the axis of a subject to be transirradiated, for example a patient. Each detector line is composed of a number of detector elements that, for example, are manufactured of a scintillator ceramic.

For readout of the signals generated by the detector elements, usually four, currently at most eight, channels are available dependent on the computing power of the computer. Dependent on the demands regarding the desired image information, a number of detector elements lying next to one another in a detector line can be respectively connected to one channel. When, for example, two or more detector elements of a detector line are connected to one channel, information about a relatively large volume excerpt of the transirradiated subject is obtained. Such an information is especially well-suited for producing high-contrast images with which, for example, it is possible to differentiate soft parts in the brain.

When, in contrast, only one detector element from each line is respectively connected to each of the channels, the transirradiated volume is small. The information thus obtained is especially well-suited for the resolution of fine structures, for example in the inner ear region.

For gating the required, fan-shaped X-ray beam, a diaphragm precedes the known detector. The provision of such a diaphragm causes increased manufacturing outlay. Moreover, the detector has a number of detector elements with a number of septa separating them. The efficiency of such a detector is not especially high. The multitude of provided detector elements further increases the manufacturing outlay of the detector.

SUMMARY OF THE INVENTION

An object of the invention is to provide a simply constructed, universal detector with enhanced efficiency for an X-ray computed tomography apparatus.

This object is achieved in a detector of the type initially described wherein the septa are arranged at both sides of a symmetry plane according to the relationship:

$$\{s_k\} = \bigcup_{m=1}^{j} \left\{ \bigcup_{p=-z/2}^{z/2} \{p \cdot n_m \cdot D_1\} \right\},$$

wherein $\{S_k\}$ is the total number of septum locations, $z \in N$ is the number of channels, $D_1$ is the smallest width of a detector element, $D_i = n_i D_1$ is the width of the $i^{th}$ subdivision, whereby $i > 1$ and $n_i > n_{i-1}$ apply, and $j \in N$ is the number of different widths $D_i$.

The term "smallest width $D_1$" mean the width of the detector element in the direction of the axis of the subject to be transirradiated, this axis generally proceeding parallel to the rotational axis of the detector. A channel is a slice of detector elements that is simultaneously processed by the measuring electronics.

The inventive relationship supplies a set of septum positions proceeding from the symmetry plane. This set corresponds to the union of sets of the septum locations for a predetermined number of widths $D_i$ the predetermined widths $D_i$ of the detector elements as well as the predetermined number z of channels.

The solution of the equation produces a minimal number of septum locations. A detector manufactured according to the inventive relationship is thus distinguished by a number of septa that is minimized for the respective application. The efficiency of such a detector is enhanced. A diaphragm at the detector can be foregone.

It is advantageous for the smallest width $D_1$ to exhibit one of the following values: g 0.5 mm, g 0.625 mm, g 1.0 mm or g 1.25 mm, whereby g is a geometry factor to which the following applies:

$$g = \frac{\text{Spacing(tube focus} - \text{detector surface)}}{\text{Spacing(tube focus} - \text{rotational center)}}$$

The term "spacing (tube focus–detector surface)" means the distance from the focus of the X-ray tube up to the surface of the detector. The term "spacing (tube focus–rotational center)' means the distance from the focus of the X-ray tube to the rotational axis of the detector.

In another embodiment that a detector line has detector elements with at least three different widths.

DESCRIPTION OF THE PREFERRED EMBODIMENTS

Figure 1:
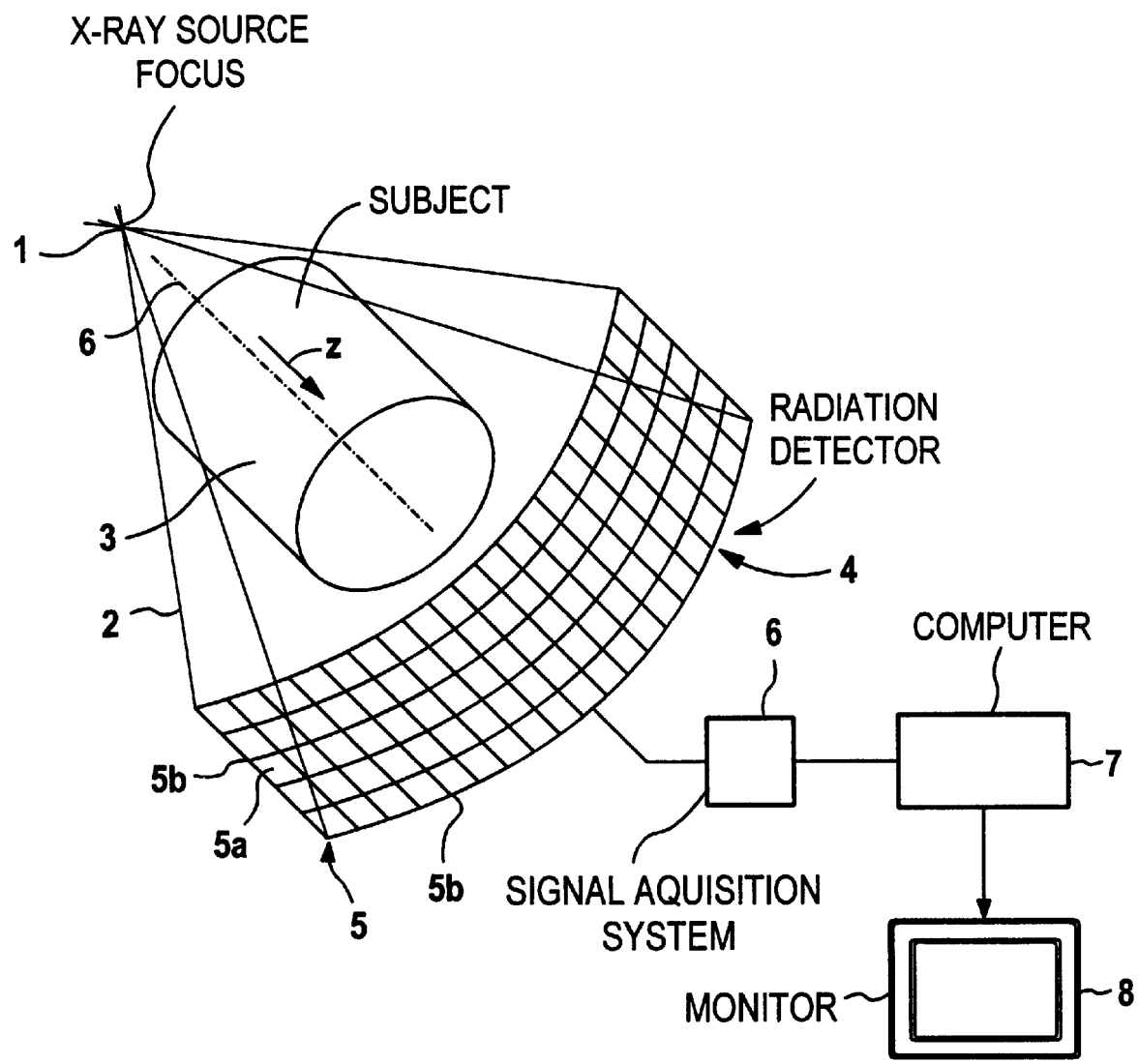
FIG. 1 shows the schematic structure of a known X-ray computed tomography apparatus in accordance with the invention.

FIG. 1 shows a focus 1 of an X-ray source from which a fan-shaped X-ray beam 2 gated by a diaphragm (not shown) emanates. This beam 2 penetrates a subject 3 and strikes a detector 4. The detector is formed of a number of parallel detector lines 5, each thereof being formed by a row of detector elements 5a. The detector elements 5a are respectively separated from one another by septa 5b.

The measuring system 1, 4 is rotatable around a rotational axis 6, so that the subject 3 is transirradiated from different projections. A signal acquisition system G reads out signals from the detector 4. A computer calculates an image of the subject 3 from the detector signals that are thereby formed, this image being reproduced on a monitor 8.

Figure 2:
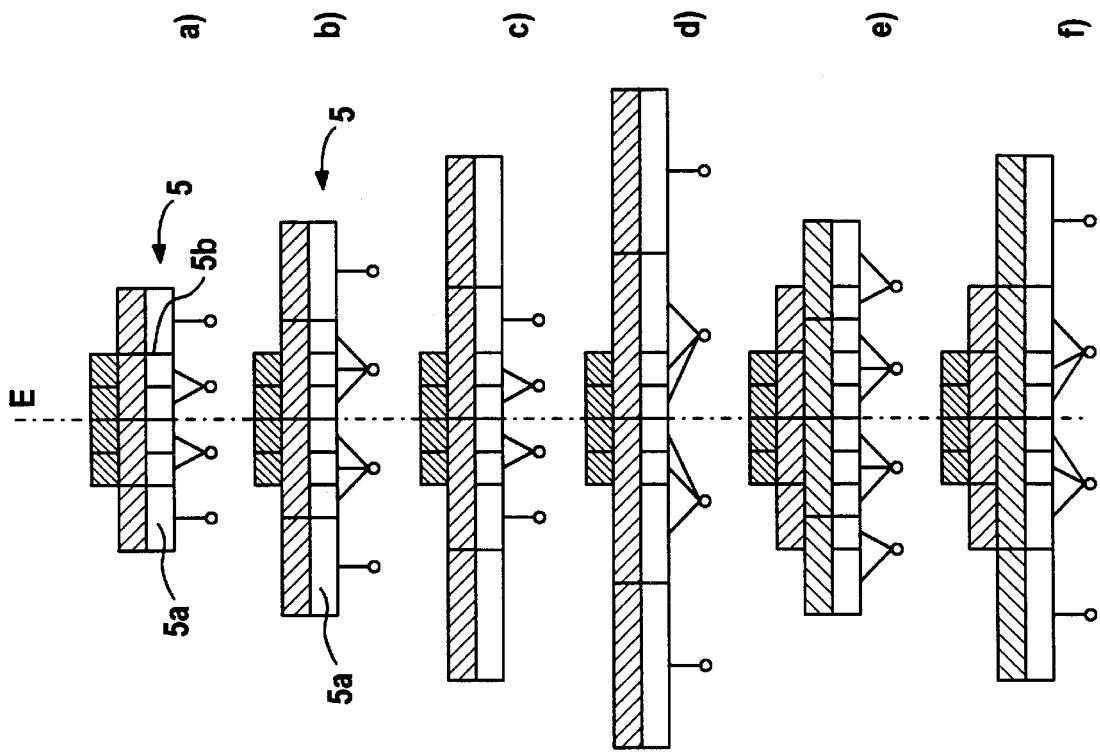
FIG. 2 shows graphic solutions of the septum arrangement for 4 channels in accordance with the invention.
Figure 3:
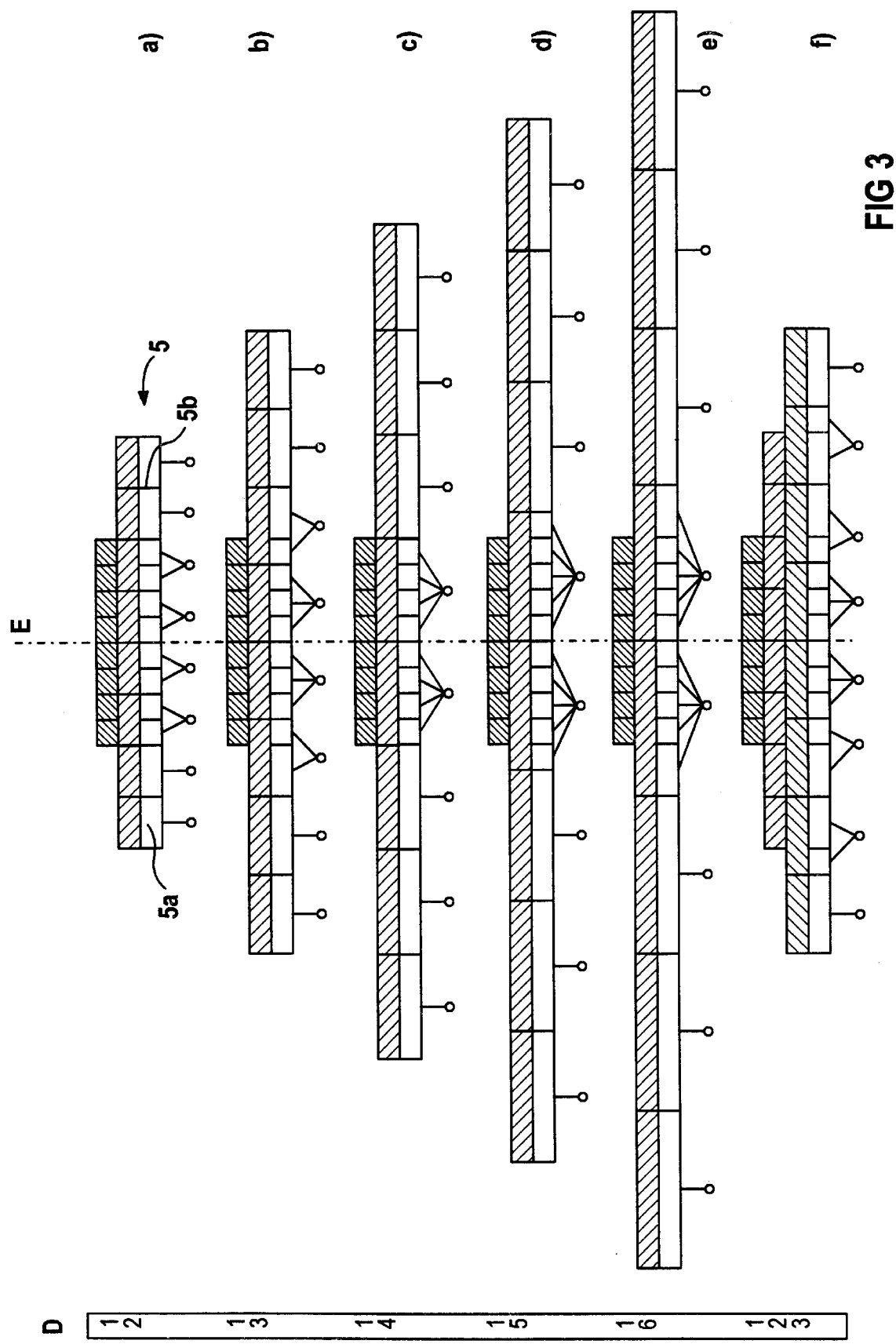
FIG. 3 shows graphic solutions of the septum arrangement for 8 channels in accordance with the invention.

Solutions of the inventive equation set forth above and how they arose are graphically shown in FIGS. 2 and 3. The lowest line, which has been left white, shows a solution of the equation for predetermined conditions.

Examples a through f of FIG. 2 show solutions for 4 channels. A symmetry plane is referenced E. It is assumed in example a that the number of different widths $D_i$ is equal to 2. A first width $D_1$ of the smallest subdivision is respectively 1. This is shown in the first line of example q with a dark underlay. A second width $D_2$ of the detector elements in example a is twice the size of the first width D1. This is shown in the second line with the gray underlay. The union of sets of the first and second line yields the arrangement of the septa 5b for the detector line 5. This is shown in the third line, left white.

According to the solution shown in example a, the detector line is constructed of six detector elements 5a. In order to enable a readout by the 4 channels, respectively 2 detector elements 5a with the small width $D_1$ are merged onto a channel. The merging is schematically indicated by the symbols under the third line.

Example b shows a graphic solution wherein the second width $D_2$ is three times the size of the first width $D_1$. It is necessary here to merge respectively three detector elements 5a of the first width $D_1$ onto a channel. In the detector line 5 respectively shown in examples c, d and f, the detector elements 5a have three different widths. Such detector lines 5 can be manufactured with a relatively large overall width without providing a large number of septa. The selection and the number of the widths D of the detector elements 5a is dependent on the particular applied purpose of the X-ray computed tomography apparatus.

The solutions in examples a through f of FIG. 3 derive in an analogous way.

Although modifications and changes may be suggested by those skilled in the art, it is the intention of the inventors to embody within the patent warranted hereon all changes and modifications as reasonably and properly come within the scope of their contribution to the art.

We claim as our invention:

1. A detector for X-ray computed tomography apparatus comprising a plurality of detector elements separated from one another by septa forming respective detector lines in a direction of a rotational axis of said tomography apparatus, said septa being symmetrically arranged with respect to a symmetry plane of each detector line that proceeds perpendicular to the rotational axis, a plurality of said detector lines being arranged next to one another, a predetermined plurality z of channels for acquiring signals generated by the detector elements with one or more of the detector elements being connectable to respective ones of said channels for acquisition of the signals, and the septa being arranged at opposite sides of the symmetry plane according to the relationship:

$$\{s_k\} = \bigcup_{m=1}^{j} \left\{ \bigcup_{p=-z/2}^{z/2} \{p \cdot n_m \cdot D_1\} \right\},$$

wherein $\{s_k\}$ is the total number of septum locations, z∈ N is the plurality of channels, $D_1$ is a smallest width of a detector element, $D_i = n_i D_1$ is a width of an $i^{th}$ subdivision, with i>1 and $n_i > n_{i-1}$, and j∈ N is the plurality of different widths $D_i$.

2. A detector as claimed in claim 1, wherein the smallest width $D_1$ exhibits a value selected from the group consisting of g 0.5 mm, g 0.625 mm, g 1.0 mm or g 1.25 mm, wherein g is a geometry factor defined as:

$$g = \frac{\text{Spacing (tube focus} - \text{detector surface)}}{\text{Spacing (tube focus} - \text{rotational center)}}.$$

3. A detector as claimed in claim 1, wherein at least one of said detector lines comprises detector elements with at least three different widths.

* * * * *